US006538136B1

United States Patent
Rizzo et al.

(10) Patent No.: US 6,538,136 B1
(45) Date of Patent: Mar. 25, 2003

(54) PREPARATION OF SUBSTITUTED PIPERIDIN-4-ONES

(75) Inventors: John Robert Rizzo, Indianapolis, IN (US); Michael Alexander Staszak, Indianapolis, IN (US); Tony Yantao Zhang, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/018,036

(22) PCT Filed: Jun. 13, 2000

(86) PCT No.: PCT/US00/15029

§ 371 (c)(1),
(2), (4) Date: Dec. 11, 2001

(87) PCT Pub. No.: WO01/00577

PCT Pub. Date: Jan. 4, 2001

Related U.S. Application Data

(60) Provisional application No. 60/141,478, filed on Jun. 29, 1999.

(51) Int. Cl.⁷ .................. C07D 211/40; C07D 211/56; C07D 211/08
(52) U.S. Cl. ............... 546/192; 546/216; 546/219
(58) Field of Search ................ 546/216, 192, 546/219

(56) References Cited

U.S. PATENT DOCUMENTS 2,883,387 A * 4/1959 Stroll et al. ................. 546/216
5,846,980 A   12/1998 Fiez-Vandal Pierre-Yves et al. ......................... 514/317

FOREIGN PATENT DOCUMENTS

DE  510184   10/1930  ................. 546/216
EP  A-982304  3/2000  ................. 546/216

OTHER PUBLICATIONS

Noller et al., "The preparation of some piperidine derivatives by the mannich reaction", J. Am. Chem. Soc., vol. 80, 1948, pp. 3853–3855 (XP000971407 Experimental table 1).

Micovic et al., "The Synthesis of Lactam Analogues of Fentanyl", J. Chem. Soc. Perkins Trans. I, 1996, pp. 2041–2047 (XP002155199 cited in the application Scheme 2, p. 2043).

* cited by examiner

Primary Examiner—Alan L. Rotman
Assistant Examiner—Raymond Covington
(74) Attorney, Agent, or Firm—Charles T. Joyner

(57) ABSTRACT

The present invention provides a novel process for the preparation of substituted piperidine-4-ones useful as intermediates in the preparation of pharmaceuticals.

13 Claims, No Drawings

PREPARATION OF SUBSTITUTED PIPERIDIN-4-ONES

This application is a 371 of PCT/US00/15029 filed Jun. 13, 2000 which claims the benefit of Ser. No. 60/141,478 filed Jun. 29, 1999.

The present invention provides a novel process for the preparation of substituted piperidin-4-ones useful as intermediates in the preparation of pharmaceuticals.

G. T. Katvalyan and E. A. Mistryukov, *Izv. Akad. Nauk SSSR, Ser. Khim.*, 11, 2575 (2436 transl.) (1968) disclose a multistep synthesis of 1-methyl-3,3-dimethyl-piperidin-4-one starting with methylamine and isobutyraldehyde. In addition, I. V. Micovic, et al., *J. Chem. Soc., Perkin Trans.*, 1, 2041 (1996) disclose a multistep synthesis of 1-benzyl-3,3-gem-dimethyl-piperdine-4-one starting with benzylamine and methyl acrylate.

It has now been discovered that 3-substituted piperidones can be prepared simply and efficiently following the one-pot procedure of the present invention, thus obviating the traditionally lengthy syntheses such as those requiring a Dieckmann condensation.

The present invention provides a process for the preparation of a compound of formula I:

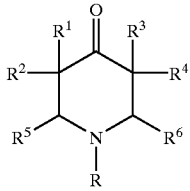

formula I wherein R is hydrogen, $C_1-C_6$ alkyl, halo($C_1-C_6$)alkyl, phenyl, benzyl, or phenyl substituted with from 1 to 3 substituents selected from the group consisting of F, Cl, Br, I, $C_1-C_6$ alkyl, $C_1-C_6$ alkoxy, halo($C_1-C_6$)alkyl, phenyl, $NO_2$, and CN; $R^1$, $R^2$, $R^3$, $R^4$, $R^5$ and $R^6$ are each independently hydrogen, $C_1-C_6$ alkyl, halo($C_1-C_6$)alkyl, phenyl, or phenyl substituted with from 1 to 3 substituents selected from the group consisting of F, Cl, Br, I, $C_1-C_6$ alkyl, $C_1-C_6$ alkoxy, —S($C_1-C_6$ alkyl), —S(phenyl), halo($C_1-C_6$)alkyl, phenyl, $NO_2$, and CN; or the pharmaceutically acceptable salt thereof; comprising combining a compound of formula II:

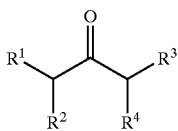

formula II wherein $R^1$, $R^2$, $R^3$, and $R^4$ are defined as above, a compound of formula III:

formula III wherein $R^5$ is defined as above, and a compound of formula IV:

R—NH$_2$   formula IV wherein R is defined as above, in the presence of a suitable acid; followed by addition of a suitable base and a compound of formula V:

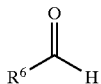

formula V wherein $R^6$ is defined as above.

As used herein, the terms "Halo", "Halide" or "Hal" refers to a chlorine, bromine, iodine or fluorine atom, unless otherwise specified herein.

As used herein, the term "Me" refers to a methyl group, the term "Et" refers to an ethyl group, the term "Pr" refers to a propyl group, the term "iPr" refers to an isopropyl group, the term "Bu" refers to a butyl group, the term "Ph" refers to a phenyl group, the term "benzyl" refers to a —CH$_2$phenyl group.

As used herein the term "$C_1-C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1-C_6$ alkyl" refers to a straight or branched, monovalent, saturated aliphatic chain of 1 to 6 carbon atoms and includes, but is not limited to, methyl, ethyl, n-propyl, isopropyl, n-butyl, isobutyl, t-butyl, n-pentyl, n-hexyl, and the like. The term "$C_1-C_6$ alkyl" includes within its scope "$C_1-C_4$ alkyl".

As used herein the term "$C_1-C_6$ alkoxy" refers to a straight or branched alkyl chain having from one to six carbon atoms attached to an oxygen atom. Typical $C_1-C_6$ alkoxy groups include methoxy, ethoxy, propoxy, isopropoxy, butoxy, t-butoxy, pentoxy and the like. The term "$C_1-C_6$ alkoxy" includes within its definition the term "$C_1-C_4$ alkoxy".

As used herein the term "—S($C_1-C_6$ alkyl)" refers to a straight or branched alkyl chain having from one to six carbon atoms attached to a sulfur atom such as —SCH$_3$, —SCH$_2$CH$_3$, —SCH$_2$CH$_2$CH$_3$, —SCH$_2$CH$_2$CH$_2$CH$_3$, and the like.

As used herein the term "halo($C_1-C_6$)alkyl" refers to a straight or branched alkyl chain having from one to six carbon atoms with 1, 2 or 3 halogen atoms attached to it. Typical halo($C_1-C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like. The term "halo($C_1-C_6$)alkyl" includes within its definition the term "halo($C_1-C_4$)alkyl".

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenyisulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formrate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, g-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

The designation ◀ refers to a bond that protrudes forward out of the plane of the page.

The designation ⋯⋯⋯ refers to a bond that protrudes backward out of the plane of the page.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of formula (I) can be prepared by one of ordinary skill in the art utilizing well known techniques and processes, such as those disclosed by Eliel and Wilen, "Stereochemistry of Organic Compounds", John Wiley & Sons, Inc., 1994, Chapter 7 Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

Compounds of formula I can be prepared by following the procedures as set forth in Scheme I. This scheme is not intended to limit the scope of the invention in any way. All substituents, unless otherwise indicated, are previously defined. The reagents and starting materials are readily available to one of ordinary skill in the art.

Scheme I

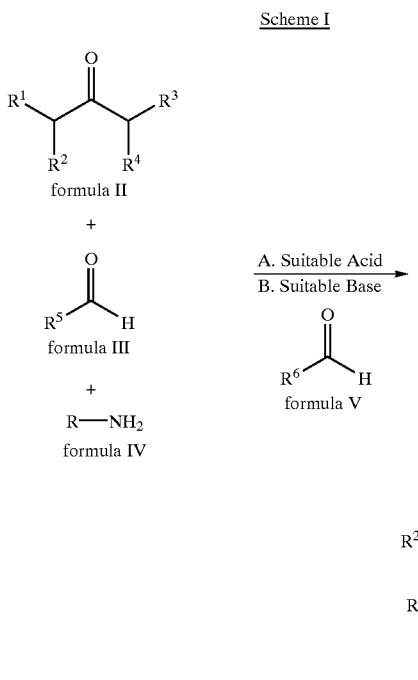

In Scheme I, step A, the compound of formula IV is combined with the compound of formula III in a suitable organic solvent, such as ethanol and the mixture is further combined with a compound of formula II in the presence of a suitable acid. Examples of a suitable acid are inorganic or organic Bronsted acids, which include, but are not limited to, hydrochloric acid, sulfuric acid, phosphoric acid, methanesulfonic acid, formic acid, trifluoroacetic acid, acetic acid, chloroacetic acid, and the like.

For example, about 2.25 equivalents of a compound of formula III is combined with a compound of formula IV in ethanol. This solution is slowly added to a solution of about 1.05 equivalents of compound of formula II in ethanol with about 1.0 to 1.2 equivalents of hydrochloric acid at a temperature of from about 50° C. to about 90° C., preferably at reflux. After 8 hours to about 24 hours, preferably about 18 hours, in Step B, a suitable base is added followed by addition of about 1 equivalent of compound of formula V. Examples of a suitable base are inorganic or organic bases well known in the art, which include but are not limited to, trialkylamines, such as triethylamine, tributylamine, diisopropylethylamine, isopropyidiethylamine, potassium hydroxide, sodium hydroxide, potassium carbonate, sodium carbonate, potassium phosphate tribasic, and the like. Alternatively, when $R^5=R^6$, all of the aldehyde can be added in one portion. The reaction is stirred at a temperature of from about 50° C. to about 80° C., preferably reflux, for about 2 hours to about 16 hours.

The compound of formula I is then isolated and purified using techniques and procedures well known in the art. For example, the reaction mixture is cooled to about 5° C. and treated with about one equivalent of base, such as potassium hydroxide dissolved in water. The mixture is then extracted with a suitable organic solvent, such as heptane and MTBE. The organic extracts are then combined, dried over anhydrous magnesium sulfate, filtered and concentrated under vacuum to provide the compound of formula I. The compound of formula I is then purified by recrystallization or flash chromatography on silica gel with a suitable eluent, such as ethyl acetate/hexane to provide purified compound of formula I. Alternatively, the salt of the product can be isolated using standard techniques well known in the art without treating with base.

The following examples represent the process of the present invention as described generally above in Scheme I. These examples are illustrative only and are not intended to limit the invention in any way. The reagents and starting materials are readily available to one of ordinary skill in the art. As used herein, the following terms have the meanings indicated: "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "EtOAc" refers to ethyl acetate; "iPrOAc" refers to isopropyl acetate; "MeOH" refers to methanol; "MTBE" refers to tert-butyl methyl ether; "TMEDA" refers to N,N,N',N'-tetramethylethylenediamine, and "RT" refers to room temperature.

EXAMPLE 1

Preparation of N-Benzyl-3,3-dimethyl-piperidin-4-one

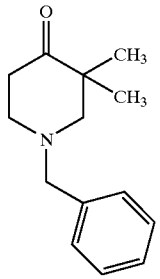

Scheme I: Benzylamine (214 g, 2 mol) is combined with formaldehyde (37% in water, 375 g, 4.5 mol) in ethanol (1 L) with occasional cooling. This biphasic mixture is added over a period of 90 minutes to a refluxing solution of 2-methyl-3-butanone (182 g, 2.11 mol) in anhydrous ethanol (1 L) and hydrochloric acid (209 g of 37% solution, 2.1 mol). The brownish solution is heated at reflux for an additional 18 hours. Then triethylamine (310 mL, 223.8 g, 2.21 mol) and formaldehyde (50 g, 36%, 0.6 mol) are added sequentially and the reaction mixture is heated at reflux for 24 hours. The reaction mixture is then cooled to 5° C. and treated with potassium hydroxide (117.6 g, 2.1 mol, dissolved in 200 mL of water). The reaction mixture is then extracted with heptane (2×500 mL) and MTBE (2×500 mL). The organic extracts is then combined, dried over anhydrous sodium sulfate, filtered and concentrated under vacuum to provide the title compound, (339.36 g after 18% by volume of the above combined organic extracts was removed prior to concentration). This material was purified by chromatography on silica gel (methylene chloride/ethanol, 100:1) to provide purified title compound.

$^1$H NMR (CDCl$_3$) δ 1.14 (s, 6H), 2.41 (s, 2H), 2.52 (t, 2H), 2.72 (t, 2H), 3.57 (s, 2H), 7.2–7.4 (m, 5H).

EXAMPLE 2

Alternative Preparation of N-Benzyl-3,3-dimethyl-piperidin-4-one

In a 1 liter 3-necked flask equipped with mechanical stirring, addition funnel and a calcium chloride drying tube is added a 37% weight solution of formaldehyde (168.5 mL, 2.25 mole) dissolved in 500 mL of absolute ethanol. The resulting solution is cooled in an ice-water bath to 10° C., and benzylamine (109 mL, 1 mole) is added dropwise over a one hour period. In a separate 3 liter 3-necked flask equipped with mechanical stirring, addition funnel and two condensers is added 3-methyl-2-butanone (113 mL, 1.06 mole) dissolved in 500 ml of absolute ethanol and concentrated hydrogen chloride (92 mL, 1.11 mole). The resulting solution is brought to reflux and the formaldehyde/benzylamine solution is added dropwise over a 2 hour period. This solution is refluxed overnight, and then cooled to ambient temperature. Diisopropylethylamine (142.2 g, 1.1 mole) and formaldehyde (22.46 mL, 0.3 mole) are added and the resulting solution is heated to reflux for six hours, and then cooled to ambient temperature. The solution is quenched with potassium hydroxide (61.6 g, 1.1 mole) in 200 mL of water, and then extracted with 500 mL ethyl acetate three times. The organics are concentrated under vacuum to give 225 g of red oil. The crude oil is dissolved in 1 liter of methylene chloride. This solution is carefully poured over 1 kg of silica gel on a sintered glass filter. The silica gel is washed with 4 L of methylene chloride. The methylene chloride is concentrated under vacuum to provide 142 g of a yellow oil which crystallizes in the freezer overnight. Yield=65.4%.

While the foregoing specification teaches the principles of the present invention, with examples provided for the purpose of illustration, it will be understood by one of the ordinary skill in the art, that the practice of the invention encompasses all of the usual variations, adaptations, or modifications, as come within the scope of the following claims and its equivalents.

What is claimed is:

1. A process for the preparation of a compound of formula I:

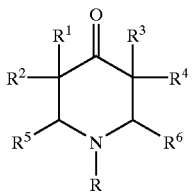

formula I wherein R is hydrogen, C$_1$–C$_6$ alkyl, halo(C$_1$–C$_6$)alkyl, phenyl, benzyl, or phenyl substituted with from 1 to 3 substituents selected from the group consisting of F, Cl, Br, I, C$_1$–C$_6$ alkyl, C$_1$–C$_6$ alkoxy, halo(C$_1$–C$_6$)alkyl, phenyl, NO$_2$, and CN; R$^1$, R$^2$, R$^3$, R$^4$, R$^5$ and R$^6$ are each independently hydrogen, C$_1$–C$_6$ alkyl, halo(C$_1$–C$_6$)alkyl, phenyl, or phenyl substituted with from 1 to 3 substituents selected from the group consisting of F, Cl, Br, I, C$_1$–C$_6$ alkyl, C$_1$–C$_6$ alkoxy, —S(C$_1$–C$_6$ alkyl), —S(phenyl), halo(C$_1$–C$_6$)alkyl, phenyl, NO$_2$, and CN; or the pharmaceutically acceptable salt thereof; comprising combining a compound of formula II:

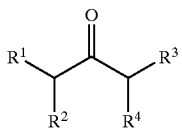

formula II wherein R$^1$, R$^2$, R$^3$, and R$^4$ are defined as above, a compound of formula III:

formula III wherein R$^5$ is defined as above, and a compound of formula IV:

R—NH$_2$     formula IV wherein R is defined as above, in the presence of a suitable acid; followed by addition of a suitable base and a compound of formula V:

formula V wherein R$^6$ is defined as above.

2. The process according to claim 1 wherein the suitable base is diisopropylethylamine.

3. The process according to claim 2 wherein the suitable acid is HCl.

4. The process according to claim 3 wherein R$^1$, R$^2$, R$^3$, R$^4$, R$^5$ and R$^6$ are each independently hydrogen, C$_1$–C$_6$ alkyl, phenyl or benzyl.

5. The process according to claim 4 wherein R$^3$ and R$^4$ are C$_1$–C$_6$ alkyl.

6. The process according to claim 4 wherein R$^5$ is C$_1$–C$_6$ alkyl and R$^6$ is hydrogen.

7. The process according to claim 5 wherein R$^3$ and R$^4$ are methyl.

8. The process according to claim 6 wherein R$^5$ is methyl.

9. The process according to claim 7 wherein R$^5$ and R$^6$ are hydrogen.

10. The process according to claim 9 wherein R$^1$ and R$^2$ are hydrogen.

11. The process according to claim 10 wherein R is hydrogen.

12. The process according to claim 10 wherein R is benzyl.

13. A process for the preparation of a compound of formula I:

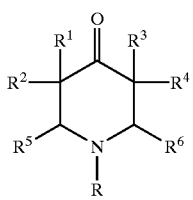

formula I wherein R is hydrogen, C$_1$–C$_6$ alkyl, halo(C$_1$–C$_6$)alkyl, phenyl, benzyl, or phenyl substituted with from 1 to 3 substituents selected from the group consisting of F, Cl, Br, I, $C_1$–$C_6$ alkyl, $C_1$–$C_6$ alkoxy, halo($C_1$–$C_6$)alkyl, phenyl, $NO_2$, and CN; $R^1$, $R^2$, $R^3$, $R^4$, $R^5$ and $R^6$ are each independently hydrogen, $C_1$–$C_6$ alkyl, halo($C_1$–$C_6$)alkyl, phenyl, or phenyl substituted with from 1 to 3 substituents selected from the group consisting of F, Cl, Br, I, $C_1$–$C_6$ alkyl, $C_1$–$C_6$ alkoxy, —S($C_1$–$C_6$ alkyl), —S(phenyl), halo($C_1$–$C_6$)alkyl, phenyl, $NO_2$, and CN; or the pharmaceutically acceptable salt thereof; comprising combining a compound of formula II:

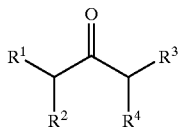

formula II wherein $R^1$, $R^2$, $R^3$, and $R^4$ are defined as above, a compound of formula III:

formula III wherein $R^5$ is defined as above, an excess of a compound of formula V:

formula V wherein $R^6$ is defined as above and $R^6$ is the same as $R^5$, and a compound of formula IV:

formula IV wherein R is defined as above, in the presence of a suitable acid; followed by addition of a suitable base.

* * * * *